United States Patent
Brown

(10) Patent No.: US 7,925,522 B2
(45) Date of Patent: *Apr. 12, 2011

(54) PERSONALIZED BODY IMAGE

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/608,110

(22) Filed: Oct. 29, 2009

(65) Prior Publication Data

US 2010/0049550 A1 Feb. 25, 2010

Related U.S. Application Data

(63) Continuation of application No. 11/610,044, filed on Dec. 13, 2006, now Pat. No. 7,613,621, which is a continuation of application No. 10/755,037, filed on Jan. 9, 2004, now Pat. No. 7,555,436, which is a continuation of application No. 09/761,337, filed on Jan. 16, 2001, now abandoned, which is a continuation of application No. 09/441,408, filed on Nov. 16, 1999, now abandoned, which is a continuation of application No. 08/784,740, filed on Jan. 16, 1997, now Pat. No. 6,032,119.

(51) Int. Cl.
*G06Q 50/00* (2006.01)
(52) U.S. Cl. .......................................... 705/3; 600/300
(58) Field of Classification Search .................. 705/2–4; 600/300
See application file for complete search history.

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |

(Continued)

FOREIGN PATENT DOCUMENTS

EP 0251520 1/1988

(Continued)

OTHER PUBLICATIONS

1975_09_00_Gardner, et al.; Comprehension and Appreciation of Humorous Material Following Brain Damage; Brain; Sep. 1975; 98(3); pp. 399-412; Dialog: File 153, Acc#02859983. (14 pages).

(Continued)

*Primary Examiner* — Gerald J. O'Connor
*Assistant Examiner* — Sind Phongsvirajati
(74) *Attorney, Agent, or Firm* — Christopher P. Maiorana, PC

(57) ABSTRACT

Delivery of health information to a patient suffering from a chronic condition is personalized by displaying the health information directly on a customized image of a body. The patient's medical record, standards of care for the condition, prescribed treatments, and patient input are applied to a generalized health model of a disease to generate a personalized health model of the patient. The personalized health model comprises an HTML file encoding an image map of a body. The body image illustrates the health condition of the individual patient. Preferably, data is collected from health provider sources and stored in a database on a server at a service provider site. The data is processed at the server, and is displayed in the patient's home using a TV connected to a multimedia processor. The multimedia processor connects the television set to a communications network such as the Internet. Applications include preventive care of chronic diseases such as diabetes and asthma.

19 Claims, 8 Drawing Sheets

U.S. PATENT DOCUMENTS

| | | |
|---|---|---|
| 3,581,072 A | 5/1971 | Nymeyer |
| 3,768,014 A | 10/1973 | Smith et al. |
| 3,808,502 A | 4/1974 | Babilius |
| 3,811,116 A | 5/1974 | Takeuchi et al. |
| 3,883,235 A | 5/1975 | Lynn et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,110,918 A | 9/1978 | James et al. |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. et al. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,625,733 A | 12/1986 | Saynajakangas |
| 4,627,445 A | 12/1986 | Garcia et al. |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,706,207 A | 11/1987 | Hennessy et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,749,354 A | 6/1988 | Kerman |
| 4,751,642 A | 6/1988 | Silva et al. |
| 4,757,022 A | 7/1988 | Shults et al. |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III |
| 4,803,625 A * | 2/1989 | Fu et al. .................. 600/483 |
| 4,835,372 A | 5/1989 | Gombrich et al. |
| 4,838,275 A | 6/1989 | Lee |
| 4,839,822 A * | 6/1989 | Dormond et al. .............. 706/45 |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 4,995,402 A | 2/1991 | Smith et al. |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,033,474 A | 7/1991 | Varelis et al. |
| 5,034,807 A | 7/1991 | Von Kohorn |
| 5,035,625 A | 7/1991 | Munson et al. |
| 5,036,462 A | 7/1991 | Kaufman et al. |
| 5,036,852 A | 8/1991 | Leishman |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,075,675 A * | 12/1991 | Barker et al. ................. 715/794 |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,137,028 A | 8/1992 | Nishimura |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,216,597 A | 6/1993 | Beckers |
| 5,219,322 A | 6/1993 | Weathers |
| 5,222,020 A | 6/1993 | Takeda |
| 5,226,431 A | 7/1993 | Bible et al. |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,277,197 A | 1/1994 | Church et al. |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |

| | | | | | |
|---|---|---|---|---|---|
| 5,307,263 A | 4/1994 | Brown | 5,596,994 A | 1/1997 | Bro |
| 5,309,919 A | 5/1994 | Snell et al. | 5,597,307 A | 1/1997 | Redford et al. |
| 5,316,008 A | 5/1994 | Suga et al. | 5,601,435 A | 2/1997 | Quy |
| 5,321,009 A | 6/1994 | Baeder et al. | 5,613,495 A | 3/1997 | Mills et al. |
| 5,325,288 A | 6/1994 | Satou | 5,619,991 A | 4/1997 | Sloane |
| 5,329,459 A | 7/1994 | Kaufman et al. | 5,624,265 A | 4/1997 | Redford et al. |
| 5,329,608 A | 7/1994 | Bocchieri et al. | 5,628,309 A | 5/1997 | Brown |
| 5,331,549 A | 7/1994 | Crawford, Jr. | 5,629,981 A | 5/1997 | Nerlikar |
| 5,331,555 A | 7/1994 | Hashimoto et al. | 5,631,844 A | 5/1997 | Margrey et al. |
| 5,333,981 A | 8/1994 | Pronovost et al. | 5,633,910 A | 5/1997 | Cohen |
| 5,335,338 A | 8/1994 | Proesel | 5,635,532 A | 6/1997 | Samid |
| 5,336,245 A | 8/1994 | Adams et al. | 5,640,569 A | 6/1997 | Miller et al. |
| 5,339,821 A | 8/1994 | Fujimoto | 5,640,953 A | 6/1997 | Bishop et al. |
| 5,341,291 A | 8/1994 | Roizen et al. | 5,642,731 A | 7/1997 | Kehr |
| 5,343,239 A | 8/1994 | Lappington et al. | 5,642,936 A | 7/1997 | Evans |
| 5,344,324 A | 9/1994 | O'Donnell et al. | 5,651,363 A | 7/1997 | Kaufman et al. |
| 5,357,427 A | 10/1994 | Langen et al. | 5,651,775 A | 7/1997 | Walker et al. |
| 5,359,509 A | 10/1994 | Little et al. | 5,659,691 A | 8/1997 | Durward et al. |
| 5,366,896 A | 11/1994 | Margrey et al. | 5,659,793 A | 8/1997 | Escobar et al. |
| 5,368,562 A | 11/1994 | Blomquist et al. | 5,664,228 A | 9/1997 | Mital |
| 5,371,687 A | 12/1994 | Holmes, II | 5,666,487 A | 9/1997 | Goodman et al. |
| 5,375,604 A | 12/1994 | Kelly et al. | 5,670,711 A | 9/1997 | Detournay et al. |
| 5,377,100 A | 12/1994 | Pope et al. | 5,675,635 A | 10/1997 | Vos et al. |
| 5,377,258 A | 12/1994 | Bro | 5,678,562 A | 10/1997 | Sellers |
| 5,381,138 A | 1/1995 | Stair et al. | 5,678,571 A | 10/1997 | Brown |
| 5,390,238 A | 2/1995 | Kirk et al. | 5,679,075 A | 10/1997 | Forrest et al. |
| 5,399,821 A | 3/1995 | Inagaki et al. | 5,680,590 A | 10/1997 | Parti |
| 5,410,471 A | 4/1995 | Alyfuku et al. | 5,680,866 A | 10/1997 | Kangas et al. |
| 5,410,474 A | 4/1995 | Fox | 5,687,322 A | 11/1997 | Deaton et al. |
| 5,429,140 A | 7/1995 | Burdea et al. | 5,687,717 A | 11/1997 | Halpern et al. |
| 5,431,690 A | 7/1995 | Schaldach et al. | 5,687,734 A | 11/1997 | Dempsey et al. |
| 5,431,691 A | 7/1995 | Snell et al. | 5,689,652 A | 11/1997 | Lupien et al. |
| 5,434,611 A | 7/1995 | Tamura | 5,692,906 A | 12/1997 | Corder |
| 5,438,607 A | 8/1995 | Przygoda, Jr. et al. | 5,704,364 A | 1/1998 | Saltzstein et al. |
| 5,438,983 A | 8/1995 | Falcone | 5,704,366 A * | 1/1998 | Tacklind et al. ............... 600/529 |
| 5,441,047 A | 8/1995 | David et al. | 5,704,902 A | 1/1998 | Vandenbelt et al. |
| 5,449,334 A | 9/1995 | Kingsbury | 5,704,922 A | 1/1998 | Brown |
| 5,454,721 A | 10/1995 | Kuch | 5,710,178 A | 1/1998 | Samid |
| 5,454,722 A | 10/1995 | Holland et al. | 5,710,918 A | 1/1998 | Lagarde et al. |
| 5,456,606 A | 10/1995 | McIntyre | 5,711,297 A | 1/1998 | Iliff |
| 5,456,692 A | 10/1995 | Smith, Jr. et al. | 5,714,319 A | 2/1998 | Joutel et al. |
| 5,458,123 A | 10/1995 | Unger | 5,715,451 A | 2/1998 | Marlin |
| 5,465,082 A | 11/1995 | Chaco | 5,715,823 A | 2/1998 | Wood et al. |
| 5,467,269 A | 11/1995 | Flaten | 5,717,739 A | 2/1998 | Dyer et al. |
| 5,471,039 A | 11/1995 | Irwin, Jr. et al. | 5,717,913 A | 2/1998 | Driscoll |
| 5,471,382 A | 11/1995 | Tallman et al. | 5,720,733 A | 2/1998 | Brown |
| 5,483,276 A | 1/1996 | Brooks et al. | 5,722,418 A | 3/1998 | Bro |
| 5,488,412 A | 1/1996 | Majeti et al. | 5,727,153 A | 3/1998 | Powell |
| 5,488,423 A | 1/1996 | Walkingshaw et al. | 5,730,124 A | 3/1998 | Yamauchi |
| 5,501,231 A | 3/1996 | Kaish | 5,730,654 A | 3/1998 | Brown |
| 5,502,636 A | 3/1996 | Clarke | 5,732,696 A | 3/1998 | Rapoport et al. |
| 5,502,726 A | 3/1996 | Fischer | 5,732,709 A | 3/1998 | Tacklind et al. |
| 5,504,519 A | 4/1996 | Remillard | 5,734,413 A | 3/1998 | Lappington et al. |
| 5,517,405 A | 5/1996 | McAndrew et al. | 5,749,083 A | 5/1998 | Koda et al. |
| 5,518,001 A | 5/1996 | Snell | 5,752,234 A | 5/1998 | Withers |
| 5,519,058 A | 5/1996 | Gonick et al. | 5,754,740 A | 5/1998 | Fukuoka et al. |
| 5,519,433 A | 5/1996 | Lappington et al. | 5,760,771 A | 6/1998 | Blonder et al. |
| 5,523,232 A | 6/1996 | Sechler | 5,772,585 A | 6/1998 | Lavin et al. |
| 5,524,637 A | 6/1996 | Erickson | 5,778,882 A | 7/1998 | Raymond et al. |
| 5,527,239 A | 6/1996 | Abbondanza | 5,782,814 A | 7/1998 | Brown et al. |
| 5,536,249 A | 7/1996 | Castellano et al. | 5,785,650 A | 7/1998 | Akasaka et al. |
| 5,542,420 A | 8/1996 | Goldman et al. | 5,787,295 A | 7/1998 | Nakao |
| 5,544,649 A | 8/1996 | David et al. | 5,791,342 A | 8/1998 | Woodard |
| 5,546,943 A | 8/1996 | Gould | 5,792,117 A | 8/1998 | Brown |
| 5,549,117 A | 8/1996 | Tacklind et al. | 5,793,969 A | 8/1998 | Kamentsky et al. |
| 5,550,575 A | 8/1996 | West et al. | 5,794,219 A | 8/1998 | Brown |
| 5,553,609 A | 9/1996 | Chen et al. | 5,794,251 A | 8/1998 | Watanabe et al. |
| 5,558,638 A | 9/1996 | Evers et al. | 5,796,393 A | 8/1998 | MacNaughton et al. |
| 5,564,429 A | 10/1996 | Bornn et al. | 5,799,318 A | 8/1998 | Cardinal et al. |
| 5,569,212 A | 10/1996 | Brown | 5,800,458 A | 9/1998 | Wingrove et al. |
| 5,572,421 A | 11/1996 | Altman et al. | 5,802,494 A | 9/1998 | Kuno |
| 5,572,646 A | 11/1996 | Kawai et al. | 5,802,534 A | 9/1998 | Hatayama et al. |
| 5,574,828 A | 11/1996 | Hayward et al. | 5,806,057 A | 9/1998 | Gormley et al. |
| 5,576,952 A | 11/1996 | Stutman et al. | 5,810,747 A | 9/1998 | Brudny et al. |
| 5,583,758 A | 12/1996 | McIlroy et al. | 5,812,983 A | 9/1998 | Kumagai |
| 5,590,648 A | 1/1997 | Mitchell et al. | 5,819,735 A | 10/1998 | Mansfield et al. |
| 5,593,349 A | 1/1997 | Miguel et al. | 5,822,544 A | 10/1998 | Chaco et al. |
| 5,593,390 A | 1/1997 | Castellano et al. | 5,822,715 A | 10/1998 | Worthington et al. |
| 5,594,637 A | 1/1997 | Eisenberg et al. | 5,825,283 A | 10/1998 | Camhi |

| | | |
|---|---|---|
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,867,821 A * | 2/1999 | Ballantyne et al. ............... 705/2 |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hoffberg et al. |
| 5,933,136 A | 8/1999 | Brown |
| 5,935,060 A | 8/1999 | Iliff |
| 5,940,801 A | 8/1999 | Brown |
| 5,941,829 A | 8/1999 | Saltzstein et al. |
| 5,945,651 A | 8/1999 | Chorosinski et al. |
| 5,950,632 A | 9/1999 | Reber et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani |
| 5,985,559 A | 11/1999 | Brown |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,029,138 A | 2/2000 | Khorasani et al. |
| 6,032,119 A | 2/2000 | Brown et al. |
| 6,035,328 A | 3/2000 | Soukal |
| 6,039,688 A | 3/2000 | Douglas et al. |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,068,615 A | 5/2000 | Brown et al. |
| 6,095,985 A | 8/2000 | Raymond et al. |
| 6,101,478 A | 8/2000 | Brown |
| 6,110,148 A | 8/2000 | Brown et al. |
| 6,113,578 A | 9/2000 | Brown |
| 6,138,145 A | 10/2000 | Kawanaka |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A | 12/2000 | Brown |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| D439,242 S | 3/2001 | Brown |
| 6,196,970 B1 | 3/2001 | Brown |
| 6,210,272 B1 | 4/2001 | Brown |
| 6,221,012 B1 | 4/2001 | Maschke et al. |
| 6,233,539 B1 | 5/2001 | Brown |
| 6,240,393 B1 | 5/2001 | Brown |
| 6,246,992 B1 | 6/2001 | Brown |
| 6,248,065 B1 | 6/2001 | Brown |
| 6,260,022 B1 | 7/2001 | Brown |
| 6,270,455 B1 | 8/2001 | Brown |
| 6,270,456 B1 | 8/2001 | Iliff |
| 6,330,426 B2 | 12/2001 | Brown et al. |
| 6,334,778 B1 | 1/2002 | Brown |
| 6,352,523 B1 | 3/2002 | Brown et al. |
| 6,368,273 B1 | 4/2002 | Brown |
| 6,370,513 B1 | 4/2002 | Kolawa et al. |
| 6,375,469 B1 | 4/2002 | Brown |
| 6,379,301 B1 | 4/2002 | Worthington et al. |
| 6,381,577 B1 | 4/2002 | Brown |
| 6,436,036 B1 | 8/2002 | Miller-Kovach et al. |
| 6,513,532 B2 | 2/2003 | Mault et al. |
| 6,849,045 B2 | 2/2005 | Iliff |
| 6,968,375 B1 | 11/2005 | Brown |
| 7,167,818 B2 | 1/2007 | Brown |
| 7,168,818 B1 | 1/2007 | Schnell |
| 7,252,636 B2 | 8/2007 | Brown |
| 7,305,348 B1 | 12/2007 | Brown |
| 2002/0019748 A1 | 2/2002 | Brown |
| 2004/0106855 A1 | 6/2004 | Brown |
| 2004/0107116 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |

FOREIGN PATENT DOCUMENTS

| | | |
|---|---|---|
| EP | 0286456 | 10/1988 |
| EP | 0320749 | 6/1989 |
| EP | 370599 | 5/1990 |
| EP | 0353046 | 10/1990 |
| EP | 0461910 | 12/1991 |
| EP | 508912 | 10/1992 |
| EP | 526166 | 2/1993 |
| EP | 0558975 | 9/1993 |
| EP | 0-653-718 A2 | 5/1995 |
| EP | 95-20199 | 7/1995 |
| EP | 680727 | 11/1995 |
| EP | 761160 | 3/1997 |
| EP | 0813155 | 12/1997 |
| GB | 2218831 | 11/1989 |
| GB | 2225637 | 6/1990 |
| JP | 5400-5785 | 1/1979 |
| JP | 54-146633 | 11/1979 |
| JP | 62-226278 | 10/1987 |
| JP | 5-155024 | 6/1993 |
| JP | 5-266002 | 10/1993 |
| JP | 7-095963 | 4/1995 |
| JP | 676709 A2 | 10/1995 |
| WO | WO-85-01667 | 4/1985 |
| WO | WO-90-00367 | 1/1990 |
| WO | WO-91-09374 | 6/1991 |
| WO | WO-93-01489 | 1/1993 |
| WO | WO-93-02622 | 2/1993 |
| WO | WO-94-16774 | 8/1994 |
| WO | WO-95-09386 | 4/1995 |
| WO | WO-95-22131 | 8/1995 |
| WO | WO-95-29447 | 11/1995 |
| WO | WO-96-07908 | 3/1996 |
| WO | WO-96-25877 | 8/1996 |
| WO | WO-96-36923 | 11/1996 |
| WO | WO-97-08605 | 3/1997 |
| WO | WO-97-12544 | 4/1997 |
| WO | WO-97-37738 | 10/1997 |
| WO | WO-98-16895 | 4/1998 |
| WO | WO-98-31275 | 7/1998 |
| WO | WO-98-39933 | 9/1998 |

OTHER PUBLICATIONS

1978_03_20_Caprihan, A., et al., A Simple Microcomputer for Biomedical Signal Processing, IECI '78 Annual Conference Proceedings on Industrial Applications of Microprocessors, (Mar. 20, 1978), 18-23.

1978_11_00_Licklider_Applications_of information_Networks_Proceedings_of_the IEEE_vol. 66_No. 11.

1980_01_00_Haynes_Geriatrics_How_to_Detect_manage_Low_Patient_Compliance_in_Chronic_illness.
1980_11_00_Haynes_Hypertension_Can_simple_Clinical_measurements_detect_patient_noncompliance.
1981_01_00_Kuykendall, V.G., et al., Assessment of Self-Monitored Blood Glucose results Using a Reflectance Meter with Memory and Microcomputer, Symposium on Computer Applications in Medical Care, (Jan. 1981), vol. 70, pp. 98-102.
1981_01_00 Soeldner, J. S., Treatment of Diabetes Mellitus by Devices, The American Journal of Medicine, (Jan. 1981), vol. 70, 183-194.
1982_01_00_Kennedy et al.; Television Computer Games: A New Look in Performance Testing; Aviat Space Environ Med; Jan. 1982, 53(1); pp. 49-53. (5 pages); Dialog Abstract: File 155, Acc#0353751.
1983_00_00_MULE. Rulebook by Electronic Arts, 1983.
1983_10_00_Mazzola, et al., Video Diabetes: A Teaching Tool or Children with Insulin-Dependent Diabetes, Proceedings—7th Annual Symposium on Computer Applications in Medical Care; Washington, DC:, Oct. 1983), File 8, Acc# 01624462.
1983_12_00 Adilman; Videogames: Knowing the Score; Creative Computing; v9; p. 224(5); Dec. 1983; Dialog: File 148, Acc# 01891055.
1985_00_00_Gauntlet (for PC) rulebook by Mindscape Inc. (Gauntlet by Apple);1985.
1985_02_00 Mims; Psychological Testing; Computers & Electronics; v23; p. 22(6); Feb. 1985; Dialog: File 47, Acc# 2654858.
1986_00_00_Physicians_Guide_Using_the_Health_Buddy_System.
1986_00_00_Thompson and Vandenberg, Clinical Biochemistry (1986) 19:255-261.
1987_06_02_US_Application_07096998_Lee_Amendment.
1987_07_00_Hunter, Technological Advances in Bedside Monitoring: Biosensors, Archives and Laboratory Medicine, (Jul. 1987), pp. 633-636.
1987_07_00_Roberts; Diabetes and Stress: A Type A Connection?, Psychology Today, (Jul. 1987), v. 21; pp. 22(1); Dialog: File 149, Acc# 05038381.
1988_00_00_Hughes_Bedside_Terminals_Clinicom_MD.
1988_00_00_Leyerle, Beverly J., et al., The PDMS as a Focal Point for Distributed Patient Data, International Journal of Clinical Monitoring and Computing, (1988), vol. 5, pp. 155-161.
1988_00_00_Yoshizawa, Daisuke, et al., The Development of a Data Processing System with Personal Computer MSX Standard System for Flow Injection Analysis, Journal of Flow Injection Analysis, (1988), V.5, No. 2, pp. 101-110.
1988_08_10_US_Application_06879900_Fu_Amendment.
1988_11_00_Douglas, A.S., et al., Hand-Held Glucose Monitor and Recorder, Proceedings of the Annual International Conference of the IEEE Engineering in Medicine and Biology Society, New Orleans, LA, (Nov. 1988), pp. 747-748.
1989_00_00_Velho et. al., Biomed. Biochim. Acta (1989) 48(11/12):957:964.
1989_05_00 Paperny_Adolescent_Pregnancy_Prevention_by_Health_Education_Computer_Games_Computer_Assisted Instruction.
1989_10_12_Diabcare Flyer Boehringer Mannheim HH101661-HH101668.
1990_00_00_Matthews, et. al., BMJ_Analysis_of_serial_measurement_in_medical_research.
1990_00_00_Miles, Laughton E., A Portable Microcomputer for Long-Term Physiological Monitoring in the Home and Work Environment, Medical Monitoring in the Home and Work Environment, (1990), pp. 47-57.
1990_00_00_Pfeiffer, E. F., The Glucose Sensor: The Missing Link in Diabetes Therapy, Hormone and Metabolic Research, (1990), vol. 24m Suppl. pp. 154-164.
1990_00_00_Schrezenmeir, J. et al., Computer Assisted Insulin Dosage Adjustment—Perspective for Diabetes Control, Hormone and Metabolic Research, Supplement Series, (1990), vol. 24, pp. 116-123.
1990_02_00_Shandle, Jack, Who Will Dominate the Desktop in the 90's? Electronics, Feb. 1990, pp. 48-50. (3 pages) Cited by 2 patents.

1991_00_00_Diabcare User Manual HH007288-HH007331.
1991_00_00_Fabietti, P.G., et al., Wearable System for Acquisition, Processing and Storage of the Signal from Amperometric Glucose Sensors, The International Journal of Artificial Organs, (1991), vol. 14, No. 3, pp. 175-178.
1991_00_00_Latman, N. S., Evaluation of Electronic, Digital Blood Glucose Monitors, Biomedical Instrumentation and Technology, (1991), vol. 25, No. 1, 43-49.
1991_00_00_Vallera, D. A., et al., Accuracy of Portable Blood Glucose Monitoring, American Journal of Clinical Pathology, (1991), vol. 95, No. 2, pp. 247-252.
1991_02_00 Billiard, A., et al. Telematic Transmission of Computerized Blood Glucose Profiles for IDDm Patients, Diabetes Care, (Feb. 1991), vol. 14, No. 2, pp. 130-134.
1991_07_23_Dept_of_Health_and_Human_Services_the_Physician_Guide _from_the_K864318_510K.
1992_00_00 Bruce, et al., The Effects of Sympathetic Nervous System Activation and Psychological Stress . . . ; Diabetologia; 35(9); 1992; 835-843; Dialog: File 5, Acc#9629427. (9 pages).
1992_00_00_Durant Medicine and Science in Sports and Exercise 24(2)265-271.
1992_00_00 _Jimison et al., Patient-Specific explanation in models of chronic disease, Revised Feb. 1992 Artificial Intelligence in Medicine 4 (1992) 191-205.
1992_04_00_Bower, Brain Clues to Energy-efficient Learning, Science News, (Apr. 1992), v. 141; p. 215(1); Dialog: File 647, Acct# 12123949.
1992_06_14_Schement, An Intelligent Controller for Neurophysiological Experiments, Proceeding of the Annual Symposium on Computer Based Medical Systems, Durham, Jun. 14-17, 1992, p. 528, line 1—p. 529, line 21.
1992_06_26_Frieberger, Paul, Video Game Takes on Diabetes Superhero 'Captain Novolin' Offers Treatment Tips, San Francisco Examiner, (Jun. 26, 1992), Fourth Edition, Business Section B1.
1992_10_00_McCullagh, PJ et al, Computerized paradigms for eliciting the contingent negative variation event-related potential, Proceedings of the Annual International Conference of the Engineering in Medicine & Biology Society, IEEE, Conf. 14, p. 2481-2483.
1992_10_05_Hauser, et al., Will Computers Replace or Complement the Diabetes Educator?, The Medical Journal of Australia, (Oct. 5, 1992), vol. 157, 489-491.
1992_11_17_07977323_Transmittal_Letter.
1993_00_00_Brunetti, P., et al., A Simulation Study on a Self-Turning Portable Controller of Blood Glucose, The International Journal of Artificial Organs, (1993), vol. 16, No. 16, pp. 51-57.
1993_00_00_Camit S Manual v3.00.
1993_00_00_Introducing the Next Generation of About Your Diabetes, U.S. Pharmacopical Convention and American Diabetes Association, (1993).
1993_00_00_Poitout, A Glucose Monitoring System for On Line Estimation in Man of Blood Glucose Concentration Using a Miniaturized Glucose Sensor Implanted in the Subcutaneous Tissue and a Wearable Control Unit, Diabetologia, (1993), vol. 36, pp. 658-663.
1993_06_00_Rose, V. L., et al., Decentralized Testing for Prothrombin Time and Activated Partial Thromboplastin Time Using a Dry Chemistry Portable Analyser, Archives of Pathology and Laboratory Medicine, (Jun. 1993), vol. 117, pp. 611-617.
1993_11_00_Furnham, et al; Measuring Locus of Control: a Critique of General Children's Health- and Work-related Locus of Control Questionnaires; British Journal of Psychology; v84 n4; p. 443(37); Nov. 1993; Dialog: File 88, Acc# 14903135.
1993_11_00_Kaufman, Steven, B., The Learning Game, Nation's Business, (Nov. 1993).
1993_12_00_Franklin; Proposed Auction Rules for PCS: The FCC Plans to Use Competitive Bidding, but Exact Procedures are Undefined; Cellular Business; v10 n13; p. 18(2); Dec. 1993; Dialog: File 148, Acc#06787310.
1993_12_02_Anonymous, Health Hero Network, Inc. Receives First-Ever FDA Clearance for Connecting Medical Devices to Internet, PR Newswire, (Dec. 2, 1993), 3 pages.

1994_00_00_Makikawa, M., et al., Microprocessor-Based Memory Device for Ambulatory Heart Rate and Physical Activity Recording, Methods of Information in Medicine, (1994), vol. 33, No. 1, pp. 94-96.
1994_02_00_Potter, David, Fundamentals of PC-Based Data Acquisition, Sensors, (Feb. 1994), pp. 12-20.
1994_03_00_Horio, Hiroyuki, et al., Clinical Telecommunication Network System for Home Monitoring, Medical & Biological Engineering & Computing, (Mar. 1994), vol. 32, 227-230.
1994_03_00_Howey, et al., A Rapidly Absorbed Analogue of Human Insulin; Diabetes, vol. 43, Mar. 1994, pp. 396-402. (7 pages).
1994_04_00_Finston, Parent + Teacher = Healthy Child, Diabetes Forecast, (Apr. 1994), v47 n9; p. 26(5); Dialog: file 149, Acc# 15804228.
1994_05_00_Szolovits_Guardian_Angel_Patient_Centered_Health_Information_Systems.
1994_07_00_Genesereth_Software_Agents.
1994_07_21_O'Donnell; Alan's At It Again; Bond Buyer; v309 n29448; p. 1(3); Jul. 21, 1994; Dialog: File 148, Acc#07478152.
1994_08_00_Valla, et al., A Structured Pictorial Questionnaire to Assess DSM-III-R-based Diagnosis in Children (6-11 years); Journal of Abnormal Child Psychology; v22 n4; p. 403(21); Aug. 1994; Dialog: File 88, Acc#15759542.
1994_10_00_Shults, Marc C., et al., A Telemetry-Instrumentation System for Monitoring Multiple Subcutaneously Implanted Glucose Sensors, IEEE Transactions on Biomedical Engineering, (Oct. 1994), vol. 41, No. 10, pp. 937-942.
1994_12_00 Wyatt, J. C., Clinical Data Systems, Part 2: Components and Techniques, Lancet, (Dec. 1994), vol. 344, No. 8937, pp. 1609-1614.
1995_00_00_Hauben, Jay R., A Brief History of the Cleveland Free-Net, available at http://www.ais.org/~irh/acn7-1.a09.html, (1995) pp. 1-4.
1995_03_00_Gordon; Auctions Become High Tech; Dealer Business; v29 n7; p. 21(4); Mar. 1995; Dialog: File 148, Acc#07862519.
1995_05_24_Onsale Onsale Brings Thrill of Auctions and Bargain Hunting Online; Unique Internet retail service debuts with weeklong charity auction for The Computer Museum in Boston, May 24, 1995; Dialog Abstract: File 610, Acc#0489267.
1995_06_05_Onsale Joins Fray as Online Shopping Picks Up Speed: Internet Booms; Computer Reseller News; Jun. 5, 1995; p. 73; Dialog: File 16, Acc#05649796.
1995_08_10_Lai_Abstraction_Models_at_System_Level_for_Networked_Interactive_Multimedia_Scripting.
1995_09_01_Lunt_The_Smart_Cards_Are_Here.
1995_10_18_Cathay Pacific Airways-USA receives more than 1,300 bids during first five days of CyberAuction; Business Wire, Oct. 18, 1995, p. 10181119.
1995_10_23_Seigmann;Nowhere to Go but Up; PC Week; v12 n42, p. A5(1); Oct. 23, 1995; Dialog: File 148, Acc#08222496.
1995_10_24 Meissner, et al., Building an Integrated Clinical and Research Network, Proceedings of the SPIE, (Oct. 24, 1995), vol. 2618, p. 92-99.
1995_10_30_Mortorala_introduces_PCMCIA28.8_Modem.
1995_11_00_Antique Collector, Putting the Lot on the Net, vol. 66, Issue 9, p. 26, Downloaded from Corporate Resource Net, Nov./Dec. 1995.
1995_11_00_Hoffman_General_Purpose_Telemetry_for_Analog_Biomedical_Signals.
1995_11_08 Edelson; Fashion Reevaluates Flickering Fortunes of TV Home Shopping; WWD; v170 n87; p1(3); Nov. 8, 1995; Dialog: File 148, Acc#08289119.
1995_12_04 RO_AUCTION Auctioneers Property Database System and RO_AUCTION Auctioneers Accounting System; RO-Auction features; Dec. 4, 1995.
1996_00_00_Theme Hospital, product review 1996 [retrieved Apr. 21, 2000], Retrieved from.
1996_00_00_Williams_Motivational_Predictors_of_Weight_Loss.
1996_01_00_Lachnit, Carroll, Hawkin's Online Auction, Photo District News, vol. 16, Issue 1, p. 18, Jan. 1996.
1996_01_11_Cheng, Joe H., PCT Search Report, (Jan. 11, 1996).
1996_Luebke, Cathy, Barrett-Jackson Auction Turns High-Tech, Business Journal, vol. 16, Issue 12, pp. 11, Jan. 19, 1996.
1996_03_08 Brenman et al.; Interaction of Nitric Oxide Synthase with the Postsynaptic Density Protein PSD-95 and a1-Syntrophin Mediated by PDZ Domains; Cell; vol. 84, pp. 757-767, Mar. 8, 1996; Ref: XP-002104701.
1996_03_08_Cathay Pacific Airways-USA to Hold First-Ever Internet CyberAuction; CyberTravelers Can Bid for 50 Business Class Round Trips to Hong Kong—No Minimum Bid; Business Wire; p. 9261084; Sep. 26, 1995; Dialog: File 148, Acc#08167091.
1996_03_13_Voelker, Rebecca, Shoe Leather Therapy is Gaining on TB, Jama, (Mar. 13, 1996), vol. 275, 743.
1996_04_00_Spitzer et al.; The moderating effect of age on self-care; Western Journal of Nursing Research, v18, n2, p. 136(13), Apr. 1996.
1996_04_22_Mam Wendy, More than just the Scores: ESPNET SportsZone is a model for expanding brand names online, InformationWeek, n576 p. 61(2), Apr. 22, 1996.
1996_04_29_Jones, Chris, Microsoft readies DocObject; technology will allow document editing in Web browsers, InfoWorld, v18 n18 p. 48(1), Apr. 29, 1996.
1996_05_20_Hutheesing, Nikhil, An on-line gamble, Forbes, v157 n10 p. 288(1), May 20, 1996.
1996_07_12_Iliff_US_Provisional_Application_60021614.
1996_08_01_United Healthcare's Optum Division goes online to better health by announcing a unique internet application. PR Newswire, p0801MNTH004. Aug. 1, 1996.
1996_08_12_Seybold—New Horizons teams with Duke, Real Media; The Seybold Report on Desktop Publishing, v10 n12 p. 24(1), Aug. 12, 1996.
1996_10_01_Research project launched to improve health of America's communities; new Disney community in Florida is focus of program. Business Wire, p. 10011142. Oct. 1, 1996.
1996_10_04_AdOptimizer—Ad Management Software for Websites, Newsbytes, pNEW10040041, Oct. 4, 1996.
1996_10_07_Telemedicine Provides Two-Way Computer Link for Parents of Very Premature Infants. PR Newswire. p. 1007NEM034. Oct. 7, 1996.
1996_11_01_Jaffrey et al.; PIN: An Associated Protein Inhibitor of Neuronal Nitric Oxide Synthase; Science; vol. 274; Nov. 1, 1996; Ref: XP 002050141.
1997_00_00_DigiPet Instruction Manual, 1997.
1997_00_00_Future of the Virtual Pet Industry, 1997 [retrieved on Apr. 23, 2000], Retrieved from.
1997_00_00_Giga Pets, 1997 [retrieved on Apr. 23, 2000], Retrieved from.
1997_00_00_Guiffrida, et al., Should We Pay the Patient? Review of Financial Incentives to enhance Patient Compliance:, Biomedical Journal, (1997), vol. 315, pp. 703-707.
1997_00_00_Kauffmann, et al., Epidemiological Study of the Genetics and Environment of Asthma, Bronchial Hyperresponsiveness and Atrophy, Am. J. Respir. Crit. Care Med., (1997), vol. 156, pp. S123-S129.
1997_00_00_Marsh, David G. Approaches Toward the Genetic Analysis of Complex Traits Asthma and Atrophy, Am. J. Respir.Crit. Care Med., (1997), vol. 156, pp. S-133-S138.
1997_00_00_Martinez, Fernando D., Complexities of the Genetics of Asthma, Am.J. Respir. Crit. Care Med., (1997), vol. 156, pp. S117-S122.
1997_00_00_Nano Page, 1997 [retrieved on Apr. 23, 2000], Retrieved from.
1997_00_00_Octhigotchi Instruction Manual, 1997. Dino-Kun Instruction Manual, 1997.
1997_00_00_Polson, Gary Recent Developments and Trends in Keychain Virtual Pets, 1997 [retrieved on Apr. 23, 2000], Retrieved from.
1997_00_00_Schork, Nicholas J., Genetics of Complex Disease, Am.J.Respir. Crit. Care Me., (1997), vol. 156, pp. S103-S109.
1997_00_00_Tamagotchi, 1997 [retrieved on Apr. 23, 2000], Retrieved from.
1997_00_00_Virtual Pet Product Reviews, 1997 [retrieved on Apr. 23, 2000], Retrieved from.

1997_04_27_Reis, H, Telemedicine: Transmitting Expertise to the Point of Care Toward an Electronic Patient Record; '97, Nashville, TN, Apr. 27-May 3, 1997, pp. 248-256, v. 3.
1997_06_12_Lacyk, John, PCT Search Report, (Jun. 12, 1997).
1997_11_18_Playmates Toys leads Americas virtual pet craze into its next generation by introducting talking Nano Pals; Talking Nano Pet Press Release; retrieved from URL http://www.virtualpet.com/vp/farm/nano/talkn/tnpress.htm on Apr. 23, 2000.
1998_00_00_Blood Glucose Monitors, Portable Health Device, (1998), vol. 17(9), pp. 253-271.
1998_00_00_Virtual Tomagutchi, 1998 [retrieved Apr. 23, 2000], Retrieved from.
1998_03_00 Fox, Not My Type: Type B Behavior, Type I Diabetes Plus Stress Equals Blood Sugar Blues, Health, (Mar. 1998), v20 n3; pp. 22(1); Dialog: File 149, Acc# 06397959.
1998_03_27_EP European Search Report, From 6858P005EP, (Mar. 27, 1998).
1998_11_00_Central Fetal Monitoring Systems with Optical Disk Storage, New Technology Brief, (Nov./Dec. 1998), vol. 2, No. 6, pp. 249-251.
1998_11_00_Updike, Stuart J., et al., Laboratory Evaluation of New Reusable Blood Glucose Sensor, Diabetes Care, (Nov./Dec. 1998), vol. 11, No. 10, pp. 801-807.
1999_07_00_Wilkins, Aaron. Expanding Internet access for health care consumers, Health Care Management Review, Summer, Jul. 24-30,1999.
1999_10_00_Moore, New Applications Break Through Storage Boundaries, Computer Technology Review, (Oct. 1999), vol. 19, No. 10 p. 1.
1999_12_01_Bruce, Health Hero Network CEO, CNNfn, Digital Jam, (Dec. 1, 1999), 3.
2000_04_23 Digital Doggie; retrieved from URL http://www.virtualpet.com/vp/farm/gigapet/ddoggie.htm Apr. 23, 2000.
2000_04_23_Giga Farm; retrieved from URL http://www.virtualpet.com/vp/farm/gigapet/gpfarm/gpfarm.htm Apr. 23, 2000.
2000_04_23_Nano Baby Instructions; retrieved from file://C:\My Documents\Nano Baby Instructions.htm Apr. 23, 2000.
2000_04_23_Nano Fighter Pets; retrieved from URL http://www.virtualpet.com/vp/farm/nano/nfighter.htm Apilr 23, 2000.
2000_04_23_Playmates Toys deals knockout blow to virtual pet competitors with introduction of Nano FighterÔ for Boys; New Nano Pet Fighting Pet Press Release; retrieved from URL http://www.virtualpet.com/vp/farm/nano/nfightpr.htm Apr. 23, 2000.
2000_04_23_Talking Nano Puppy; retrieved from URL http://www.virtualpet.com/vp/farm/nano/talkn/talkn.htm Apr. 23, 2000.
2000_06_14_Towards a partnership of care, M2 Presswire, Jun. 14, 2000.
2001_09_24_09300856_AMENDMENT.
2002_03_11_Schenkels, P., Supplementary European Search Report, Application No. EP 97 92 2716, (Mar. 11, 2002).
2002_09_28_How Flash Memory Works, Internet printout of URL address: http://www.howstuffworks.com/flash-memory4.htm, (Sep. 28, 2002), 2 pages.
2003_04_21_09422046_Amendment_with_Affidavit.
2004_02_13_Tandy Radio Shack , The description of the Tandy Radio Shack TRS-80 Model 100/102 device available at http://www.old-computuers.com/musuem/computer.asp?c=233, World Wide Web, (Feb. 13, 2004), 1-3.
2005_06_13_11150145_Amendment.
2006_03_29_11150145_OA.
2006_06_19_09237194_Office_Actions_Response.
2006_06_26_11150145_Amendment.
2006_08_17_Abbott_Amended_Complaint.
2006_08_17_Abbott_v_Dexcom_06-514.
2006_08_17_Request_for_Re-examination_5899855_90008234.
2006_09_21_09237194_Declation_of Stephen_Brown_with_Attached_Exhibits_Y_and_Z_thereof.
2006_09_22_11150145_OA.
2006_09_27_09422046_Office_Actions_Response.
2006_10_27_11150145_Amendment.
2007_01_04_11150145_Amendment.
2007_05_09_Leapfrog_v_Fisher_Price.
2007_10_29_Request_for_Re-examination_5899855_90008909.
2007_11_09_Request_for_Re-examination_7223236_90010053.
2007_11_15_Request_for_Re-examination_7223236_90010053.
2008_01_25_Dept_of_Health_and_Human_Services_The_Physicians_Guide_Become_publicly_Available.
2008_06_20_09422046_OA.
2008_06_20_Alere_First_Supplemental_Response_to_Plaintiff_Interrogatories.
2008_08_01_Excerpts_from_the_Prosecution_History_for_US_Patent_5899855.
2008_08_01_Inter_Party_Re-Exam_7223236_95000386.
2008_08_01_Request_for_Re-examination_5601435_90009237.
2008_08_01_Request_for_Re-examination_5879163_90009238.
2008_08_01_Request_for_Re-examination_6151586_90009240.
2008_08_01_Request_for_Re-examination_6161095_90009239.
2008_08_01_Request_for_Re-examination_7223236_95000386.
2008_09_23_Request_for_Re-Examination_6368273_90009281.
2008_12_04_Request_for_Re-Examination_5899855_90009352.
2008_12_10_Alere_Second_Supplemental_Response_to_Plaintiff Interrogatories.
2008_12_10_Alere_Second_Supplemental_Response_to_Plaintiff Interrogatories_Exhibit_1.
2008_12_10_Alere_Second_Supplemental_Response_to_Plaintiff_Interrogatories_Exhibit_2.
2008_12_10_Alere_Second_Supplemental_Response_to_Plaintiff_Interrogatories_Exhibit_3.
2008_12_10_Alere_Second_Supplemental_Response_to_Plaintiff_Interrogatories_Exhibit_4.
2008_12_10_Alere_Second_Supplemental_Response_to_Plaintiff_Interrogatories_Exhibit_5.
2008_12_10_Alere_Second_Supplemental_Response_to_Plaintiff_Interrogatories_Exhibi_t6.
2008_12_10_Alere_Second_Supplemental_Response_to_Plaintiff_Interrogatories_Exhibit_7.
2008_12_10_Alere_Second_Supplemental_Response_to_Plaintiff Interrogatories_Exhibit_8.
2008_12_10_Alere_Second_Supplemental_Response_to_Plaintiff Interrogatories_Exhibit_8A.
2008_12_10_Alere_Second_Supplemental_Response_to_Plaintiff Interrogatories_Exhibit_9.
2008_12_10_Alere_Second_Supplemental_Response_to_Plaintiff Interrogatories_Exhibit_B.

* cited by examiner

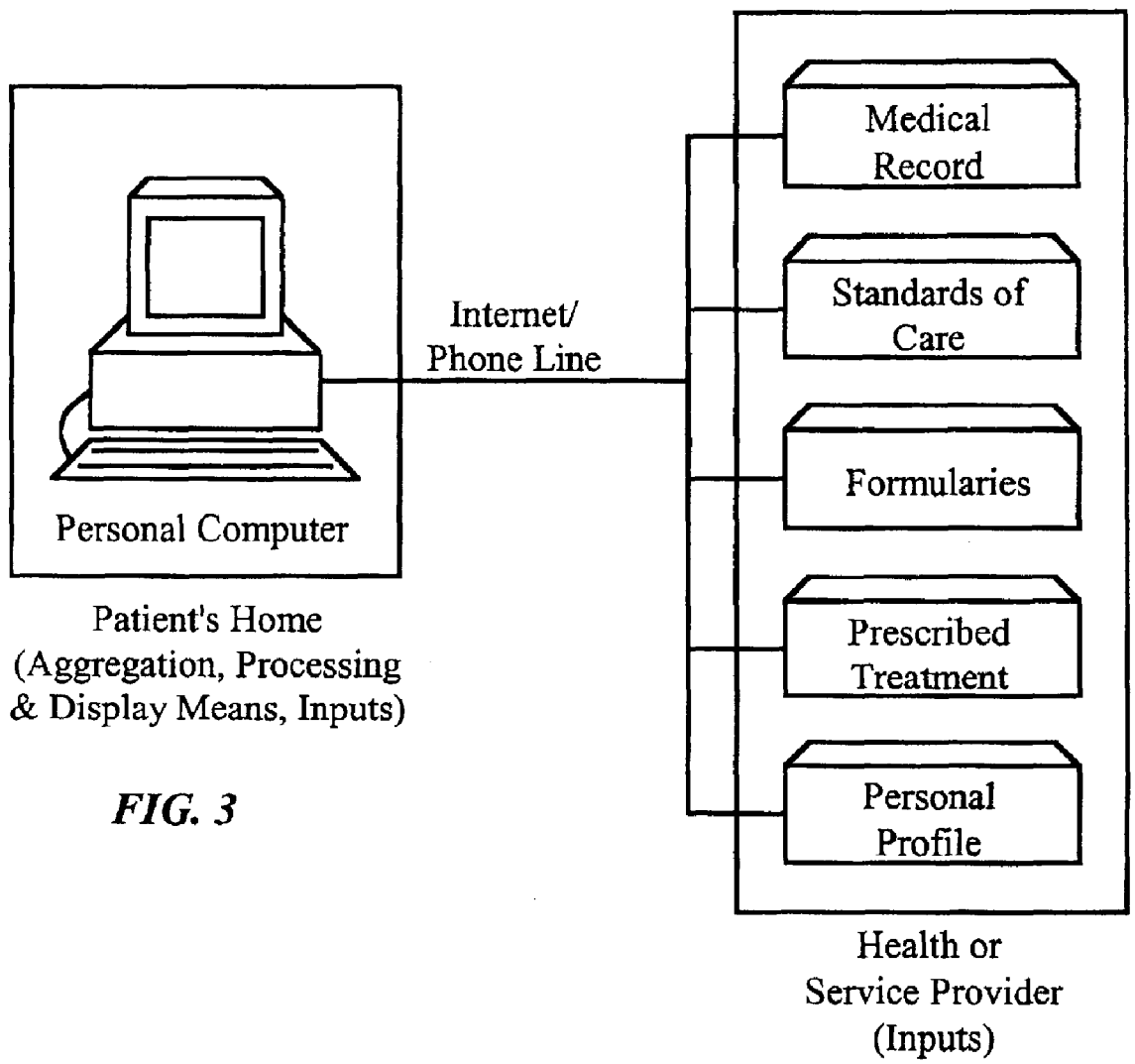
*FIG. 3*
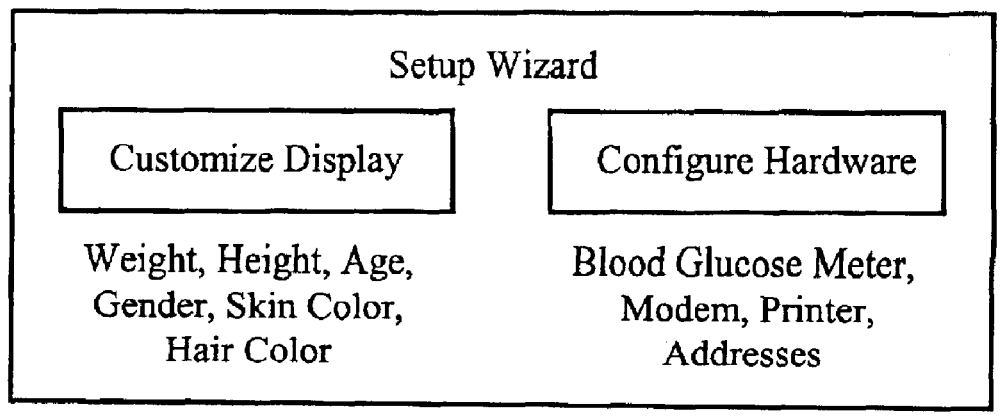
*FIG. 4-A*

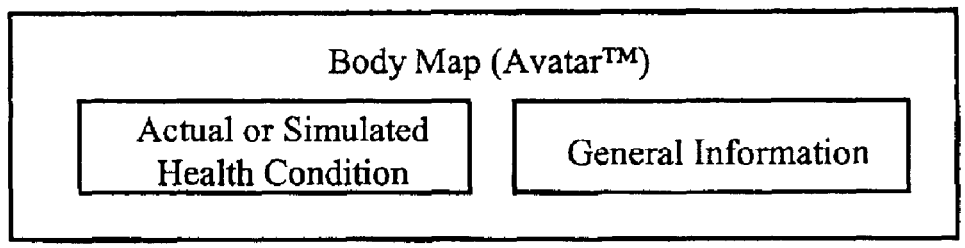
FIG. 4-B
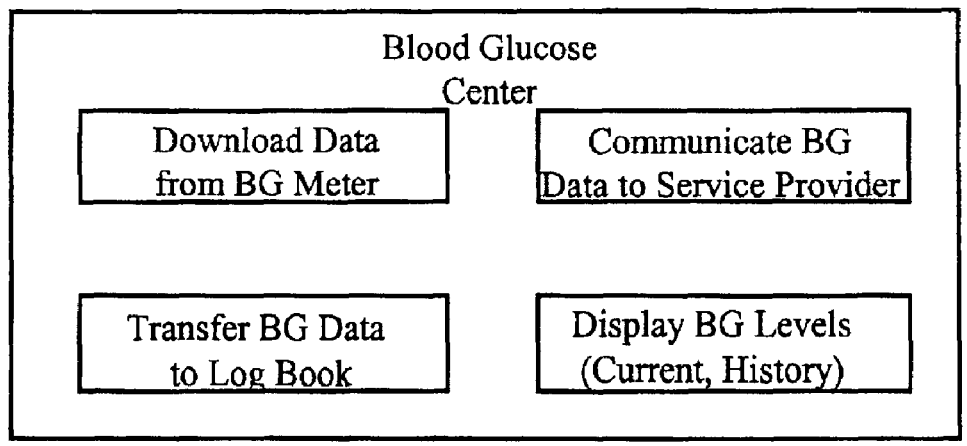
FIG. 4-C
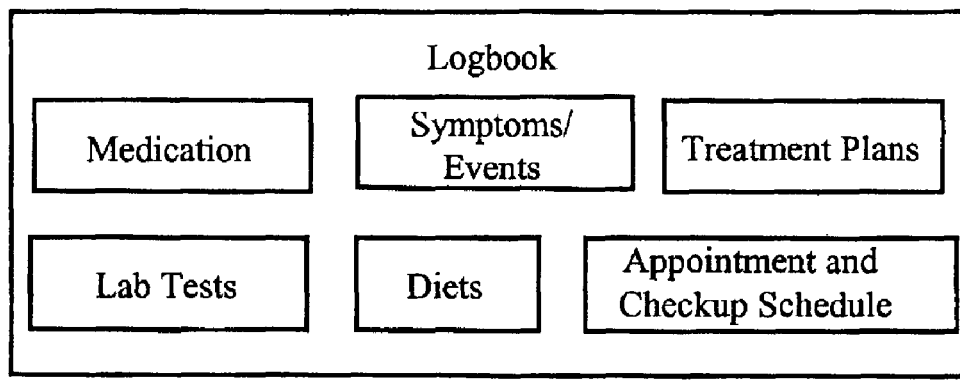
FIG. 4-D
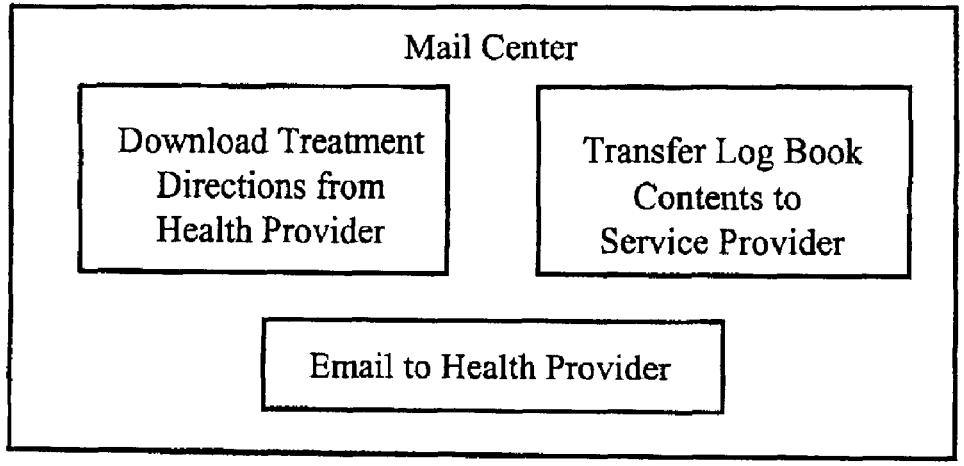
FIG. 4-E

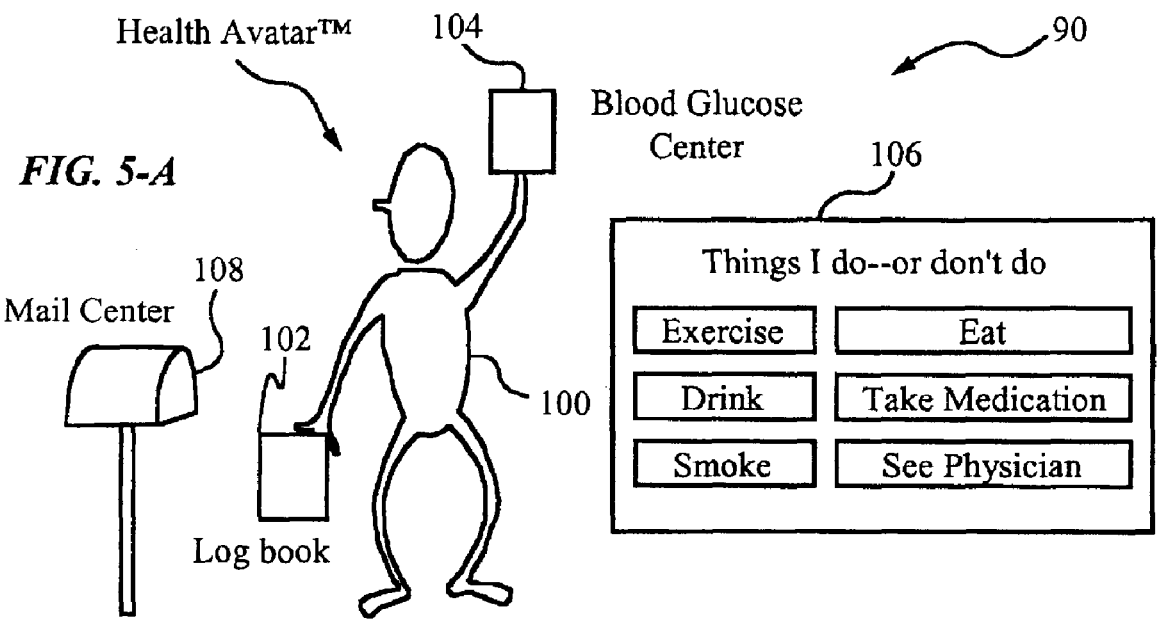
FIG. 5-A
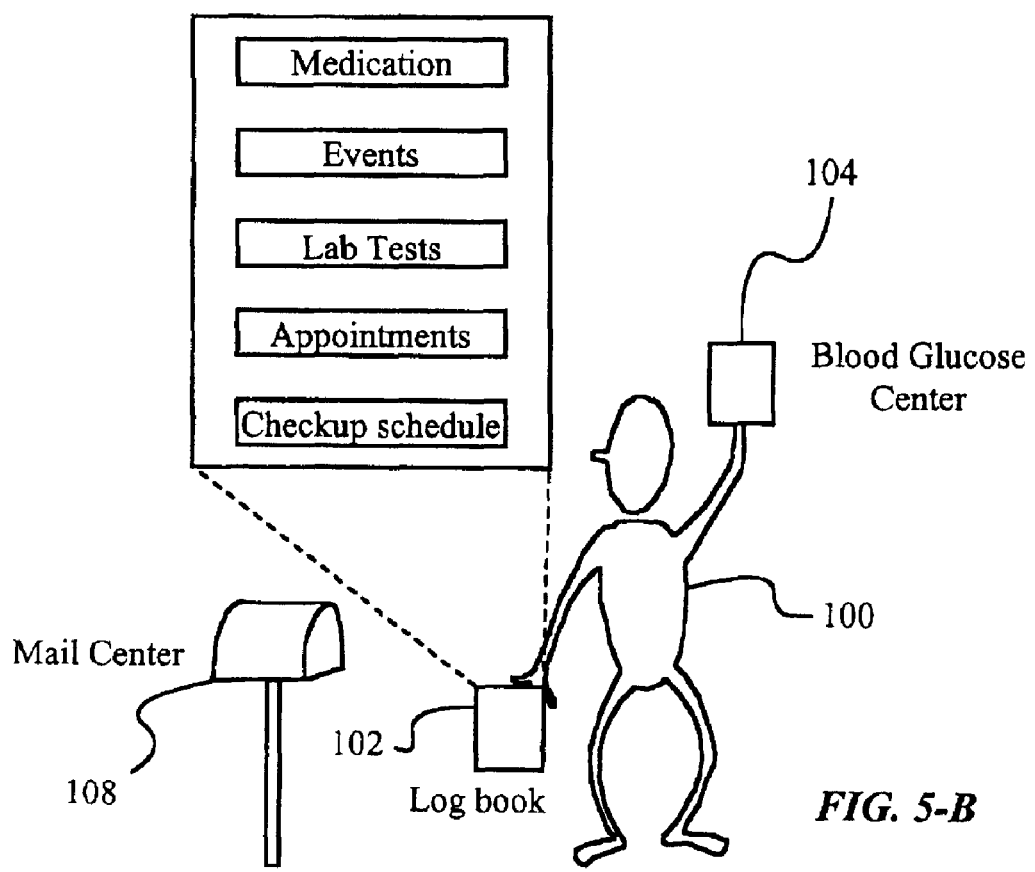
FIG. 5-B

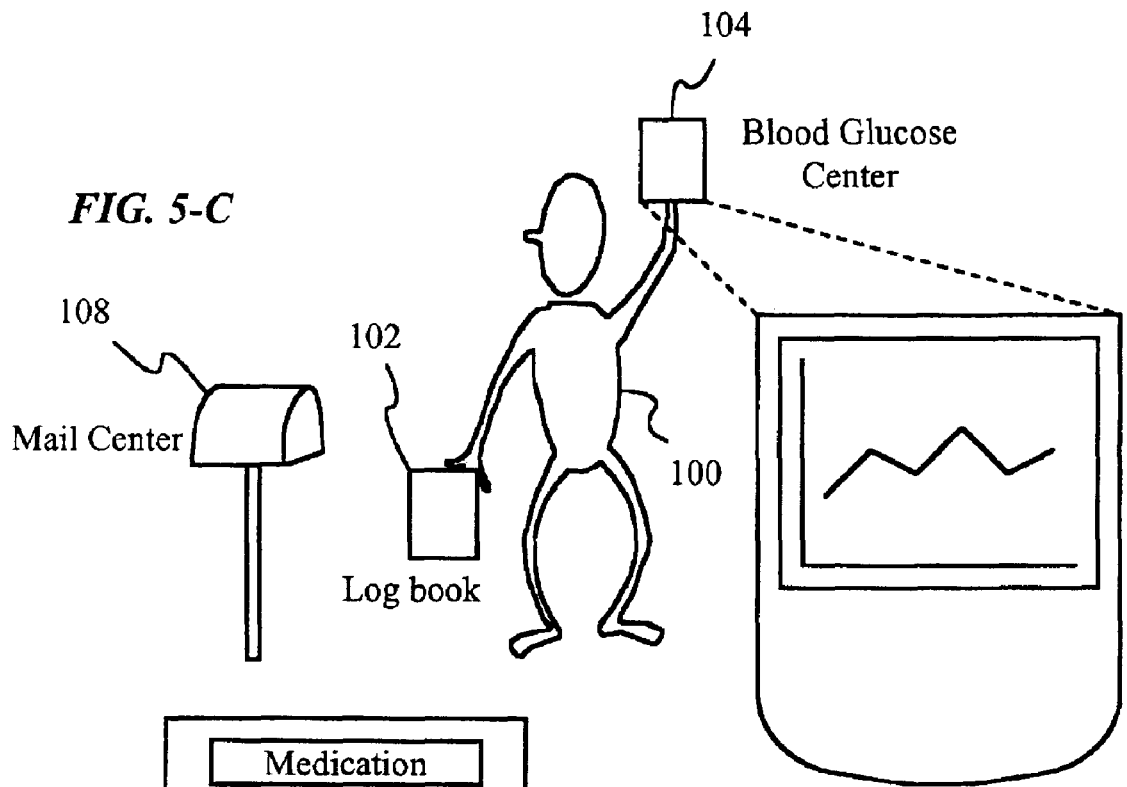
*FIG. 5-C*
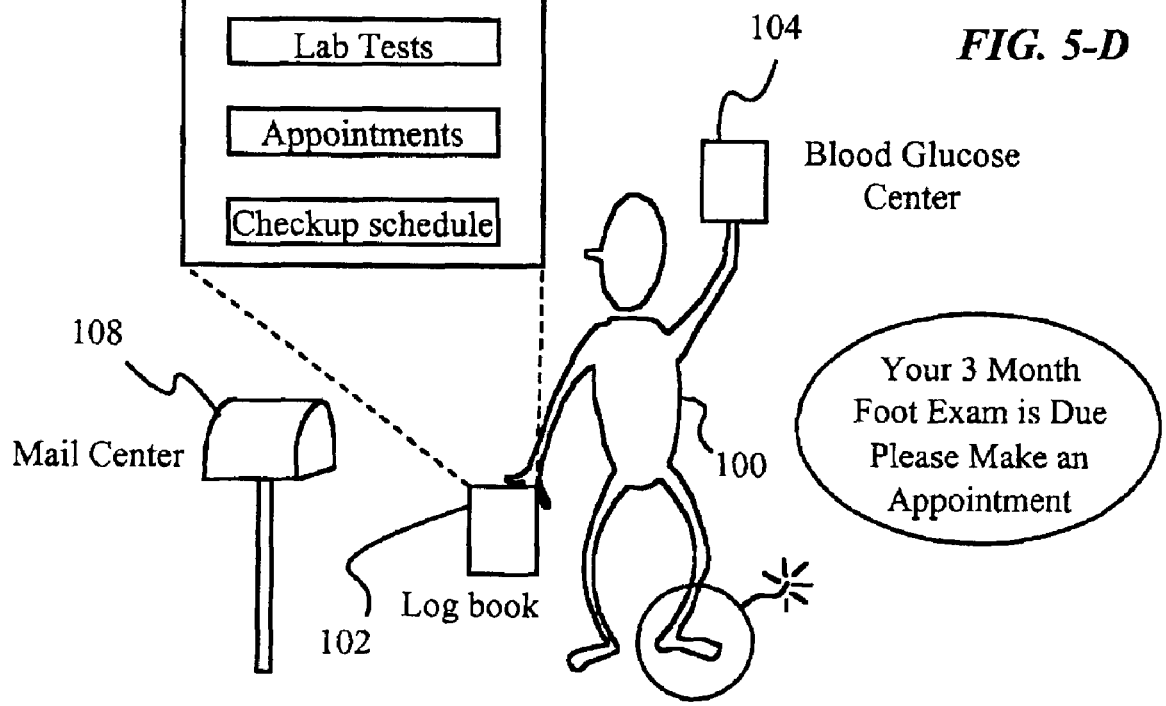
*FIG. 5-D*

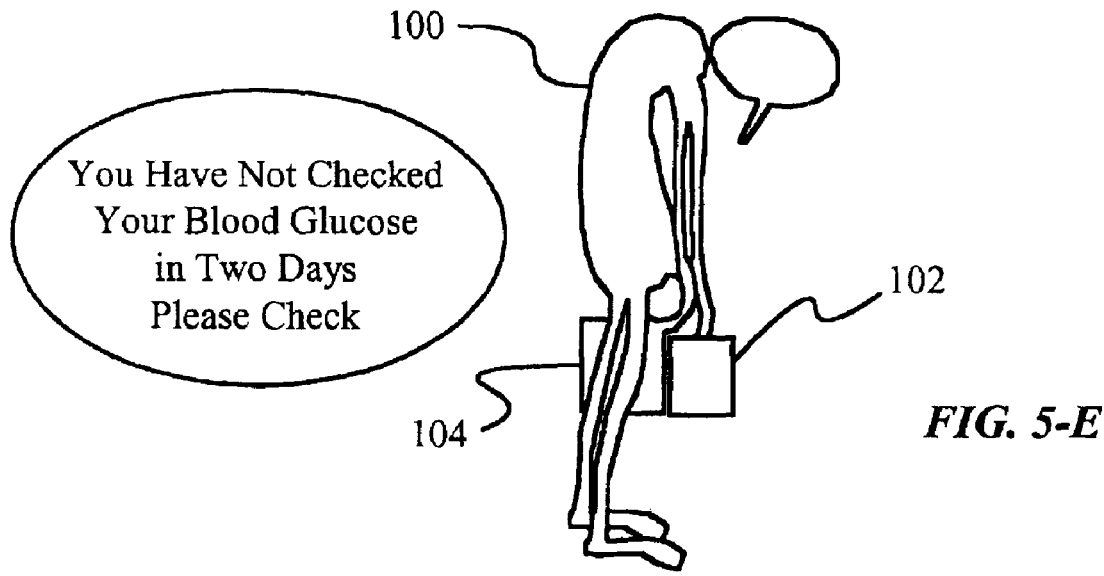
*FIG. 5-E*
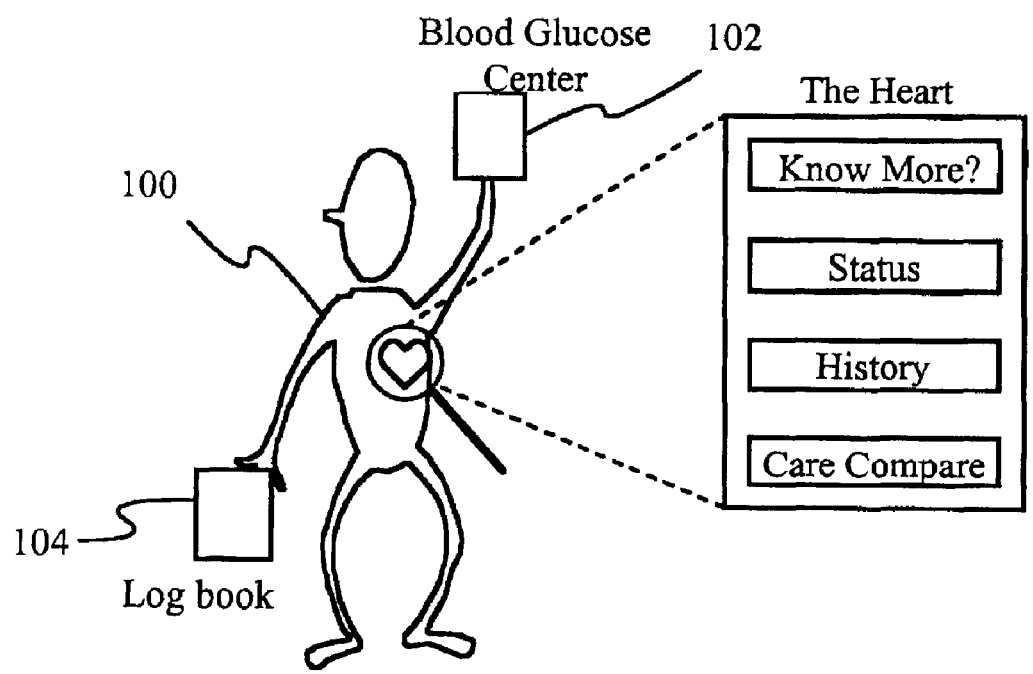
*FIG. 5-F*

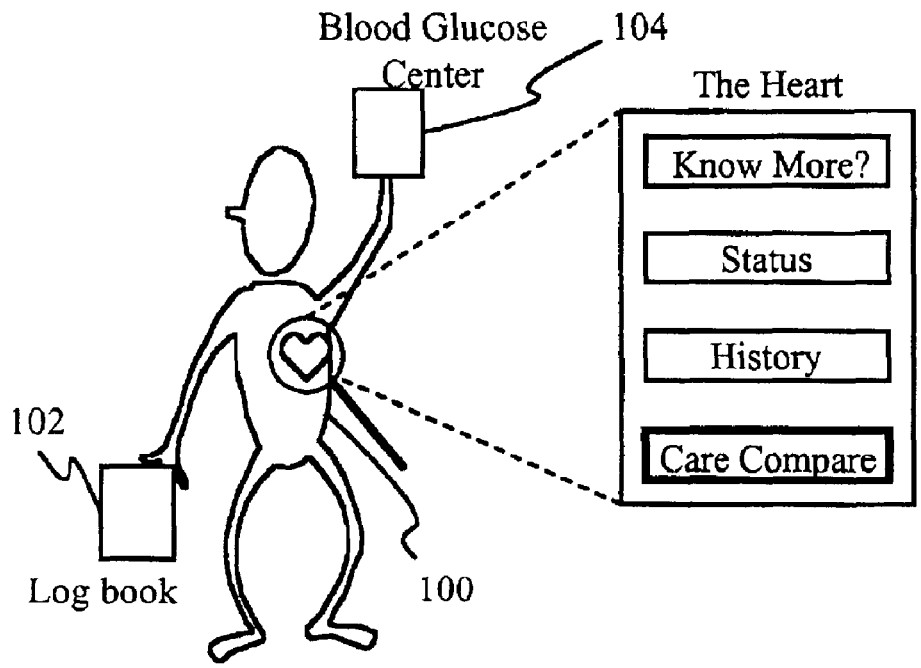

FIG. 5-G

You have searched the database for TESTS done in relation to DIABETES and HEART

1. Heart Exam
43% of people with Diabetes had no heart exam performed in one year.

57% of people with Diabetes had at least one heart exam performed in one year.

More Information?
Press Here for detailed info about the test, including the ADA's recommendations for tests in people with diabetes.

PERSONALIZED BODY IMAGE

CONTINUATION APPLICATION DATA

This application is a continuation of U.S. Ser. No. 11/610,044, filed Dec. 13, 2006, now U.S. Pat. No. 7,613,621 which is a continuation of U.S. Ser. No. 10/755,037, filed Jan. 9, 2004, now U.S. Pat. No. 7,555,436 which is a continuation of U.S. Ser. No. 09/761,337, filed Jan. 16, 2001, now abandoned, which is a continuation of U.S. Ser. No. 09/441,408, filed Nov. 16, 1999, now abandoned, which is a continuation of U.S. Ser. No. 08/784,740, filed Jan. 16, 1997, now U.S. Pat. No. 6,032,119, issued Feb. 29, 2000, each of which are incorporated by reference.

FIELD OF THE INVENTION

This invention relates to computer systems for managing health care, and in particular to a system and method for displaying personalized health information to a patient having a chronic disease or health condition.

BACKGROUND OF THE INVENTION

The health care community has recognized in recent years the importance of prevention care in managing patients' health. Preventive care is particularly important in managing the health of patients having chronic diseases or long-term conditions. Preventive care includes educating patients about their disease, ensuring communication between patients and health care providers (e.g., doctors), and providing patients with tools and/or treatments for managing their disease.

Commonly used preventive care approaches suffer from several drawbacks. Much of health care is voluntary, and thus a large fraction of health care resources is typically spent on patients who are actively seek involvement in their care. A large number of patients do not actively seek information and treatment in the absence of symptoms, however. Also, health providers receive very little information on whether patients are complying with preventive care guidelines. Thus, health providers often are not able to take remedial steps before the disease affects the patients symptomatically (e.g., through pain). Reaching passive patients is thus critical to delivering effective preventive care.

The mass-marketing techniques used for health education by most health maintenance organizations (HMOs) and insurance companies allow little customization of information to an individual patient's needs. Consequently, many patients may not directly identify with the educational approaches used by their health providers. Personalizing health education would significantly raise the effectiveness of preventive care, especially in children and adolescents.

U.S. Pat. No. 5,549,117 describes a system for communicating health information between health providers and patients having a chronic disease such as asthma. A patient unit displays health information, and communicates health information between the patient and a health provider. The display is relatively impersonal, however.

OBJECTS AND ADVANTAGES OF THE INVENTION

It is a primary object of the present invention to provide a personalized display of a health condition of a patient, such that the patient identifies with the display. It is another object of this invention to provide a method of motivating a patient to follow a prescribed treatment regimen. It is yet another object of this invention to provide a health data display that can be easily comprehended. It is still another object of this invention to provide a system and method for involving patients in their own care, for providing feedback to patients about their health condition, and for monitoring patients' progress in managing their health condition.

SUMMARY OF THE INVENTION

A system of the present invention comprises a set of inputs, a processing means in communication with the inputs, and a display means in communication with the processing means. The set of inputs generate a set of data $\{D[j]\}$, $j=1 \ldots J$. A datum $D[j]$ of the set $\{D[j]\}$ characterizes a personal health condition of a patient. The processing means generates a personalized health model of the patient from a generalized health model of the patient and from the data set $\{D[j]\}$. The display means generates a display comprising a body image. The body image illustrates the personalized health model.

The personalized health model is a parameterized model of the health of the individual patient under treatment. The personalized health model is defined by a set of parameters $\{P[k]\}$, $k=1 \ldots K$. The generalized health model is a model of the disease or condition under treatment. The generalized health model is defined by a set of functions $\{f[k]\}$ that specify the dependence of $\{P[k]\}$ on $\{D[j]\}$. That is, $P[k]=f[k](\{D[j]\})$ for all k. The processing means assigns values to the parameters $\{P[k]\}$ using the data $\{D[j]\}$. Parameters suitable for characterizing various diseases include condition of a body part/organ, blood glucose level, respiratory flow, blood pressure, cholesterol level, patient weight, T-cell count, and frequency of health episodes.

The set of inputs comprises a medical record of the patient, as well as records of: a standard of care for the general health condition or disease of the patient, a prescribed treatment of the patient, a display preference, a personal profile of the patient. The set of inputs further comprises a patient identification means (preferably a card) connected to the display means. The patient identification means specifies the identity of the patient corresponding to a particular display. The patient identification means also specifies a prescribed treatment of the patient and an address of the processing means, allowing a communication between the display means and the processing means. The set of inputs also comprises a patient feedback means (preferably a keyboard) in communication with the processing means, for allowing the patient to communicate a subset of feedback data to the processing means. The feedback means also allows the patient to enter a subset of simulation data characterizing a simulated personal health condition of the patient.

The display means preferably comprises a television set, and a multimedia processor for connecting the television set to the processing means. The display comprises a section assigned to a parameter P[k]. In particular, the body image comprises a section assigned to a parameter P[k]. A set of characteristics of the body image match a set of predetermined physical characteristics, such that the patient is able to customize the appearance of the body image. Such physical characteristics include age, height, gender, weight, skin color, and hair color. In a particular embodiment, the body image comprises a reproduction of an image of the patient (e.g., a photograph of the patient). In another embodiment, the body image comprises an image of a fictional character.

Preferably, the processing means is in communication with the display means over a remote network, such that the processing means is able to handle processing for multiple display means located at different patient locations. The processing means is in communication with at least some of the inputs over a remote network. Processing means at a service provider location can thus access inputs at a health care provider location. A data aggregation means (preferably a database) is in communication with at least some of the inputs and with the processing means. The data aggregation means collects a subset of the data set {D[j]} from the set of inputs, allowing a reduction in the number of direct connections between the processing means and the inputs. The data aggregation means is in communication with the display means over a remote network, so that the data aggregation means stores data for multiple patients.

DESCRIPTION OF THE FIGURES

FIG. 3 shows an alternative architecture of a system of the present invention.

FIG. 4-A depicts the functions of a setup wizard in an embodiment of the present invention.

FIG. 4-B illustrates the functions of a body image module of the present invention.

FIG. 4-C shows the functions of a blood glucose center module of the present invention.

FIG. 4-D shows the functions of a logbook module of the present invention.

FIG. 4-E shows the functions of a mail center module of the present invention.

FIG. 5-A illustrates schematically an introductory screen shot for a diabetes treatment system of the present invention.

FIG. 5-B illustrates the display resulting from the patient's accessing the log book section of the display of FIG. 5-A.

FIG. 5-C illustrates the display resulting from the patient's accessing a subsection of the blood glucose center section of the display of FIG. 5-A.

FIG. 5-D shows a warning resulting from the patient's failure to have a timely foot checkup, according to the system illustrated in FIG. 5-A.

FIG. 5-E shows a warning resulting from a patient's failure to check a blood glucose level according to the patient's treatment plan, according to the system illustrated in FIG. 5-A.

FIG. 5-F shows the display of the system illustrated in FIG. 5-A following the patient's accessing of a display subsection corresponding to the heart.

FIG. 5-G shows the display of the system illustrated in FIG. 5-F following a patient request for comparative care information on the heart.

DETAILED DESCRIPTION

In the ensuing description, the notation {A[j]} is understood to refer to a set of A[j], for j taking some values between a minimum value 1 and a maximum value J. The notation A[j] is understood to refer to some (fixed) j.

Figure 1:
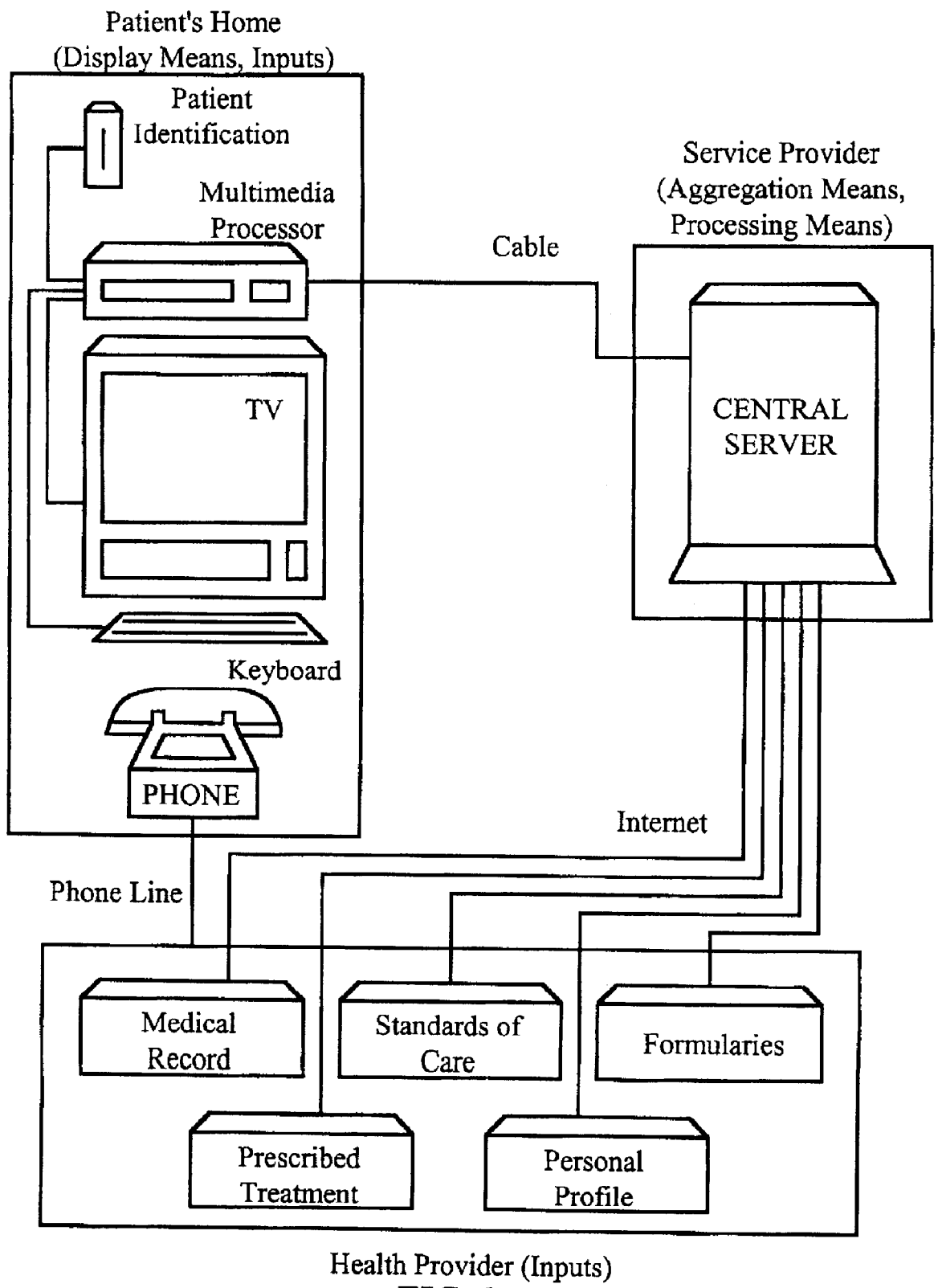
FIG. 1 shows the architecture of a system for health information delivery in a preferred embodiment of the present invention.

FIG. 1 is a schematic diagram illustrating a preferred architecture for a system of the present invention. A processing means (preferably computer software) located on a central server is in communication over remote communication networks with a display means and a set of inputs. The central server processes information for multiple patients, and is thus capable of communicating with multiple display means and input locations. The central server comprises a data aggregation means, preferably a database, in communication with the set of inputs and with the processing means. The data aggregation means collects a subset of the data set {D[j]} from the inputs. Data collected by the data aggregation means is accessed by the processing means. The display means is located at the patient's home. Preferably, the central server is in communication with the health provider over the Internet, and with the patient's home over a cable television delivery line.

The display means preferably comprises a conventional television receiver, and a means for connecting the TV set to a communications network, as illustrated in FIG. 1. Preferably, the TV set is connected to the Internet via a multimedia processor such as a WebTV™ Internet Terminal from WebTV Networks (distributed by Sony). The multimedia processor is in communication over a remote network (such as the Internet, a phone line, or cable used for delivery of cable television programming) with a server at a service provider location.

The multimedia processor connects the processing means on the central server to inputs located at the patient's home: a patient feedback means preferably comprising a keyboard, and a patient identification means preferably comprising a data-bearing card, or "smart card". The multimedia processor has a receiving slot for receiving the patient identification smart card. The patient identification card contains an encrypted patient code, a prescribed treatment for the patient, and a URL address of the processing means. The keyboard allows the patient to provide a subset of feedback data, including display preferences specifying a formatting of the display.

The set of inputs further comprises inputs located at a health care provider location, including records of: a medical history of the patient, a standard of care for a general health condition or disease of the patient, a prescribed treatment for the patient, and a personal profile of the patient. The above-incorporated U.S. patent application Ser. No. 08/732,158 entitled "Multiple Patient Monitoring System for Proactive Health Management" contains further information on data available to the health care provider.

Examples of data specified by the inputs include blood glucose level histories, generally acceptable blood glucose levels, dates of doctor examinations, generally recommended time periods between doctor examinations, ratings of the patient's interest for a cultural subject (e.g., sports, music), and display customization variables entered by the patient.

Figure 2:
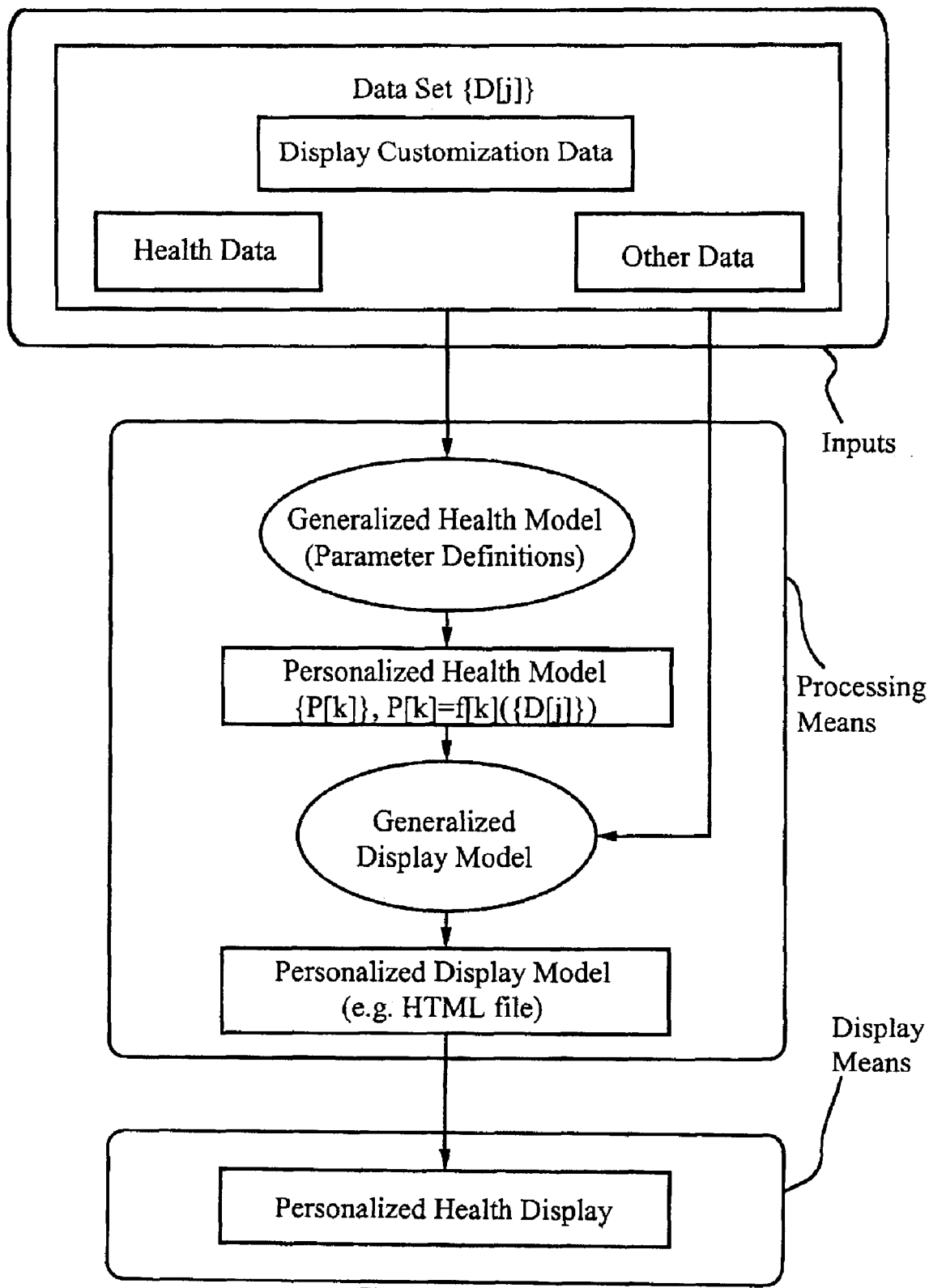
FIG. 2 illustrates processing steps performed on medical and other data to generate a personalized display of the present invention.

FIG. 2 illustrates generally the processing steps performed on the data {D[j]}. A personalized health model of the patient is generated from a generalized health model of the patient's health condition and the patient-specific data {D[j]}. The personalized health model characterizes the patient's current health condition. The personalized health model is defined by a set of parameters {P[k]}, k=1 ... K. In a preferred embodiment designed for diabetes preventive care, suitable parameters include blood glucose level, conditions of body parts or organs (e.g., heart, feet), and compliance with treatment and/or monitoring protocols. Parameters suitable for the characterization of other diseases include respiratory flow in asthma, blood pressure in hypertension, cholesterol in cardiovascular disease, weight in eating disorders, T-cell or viral count in HIV, and frequency or timing of episodes in mental health disorders.

The generalized health model specifies the dependence of the values {P[k]} on the data {D[j]}. The dependence is determined by a set of functions {f[k]}, where P[k]=f[k]({D[j]}) for all k. That is, the value P[k] of the kth parameter is specified in general by a function f[k]. The function f[k] has as its argument the set of data {D[j]}, i.e. f[k] depends on at least one datum D[j]. The forms of the functions {f[k]} can be readily determined by the skilled artisan according to the disease under treatment.

For example, parameter P[1] may measure the latest recorded blood glucose level of the patient, and the datum D[1] may be the latest blood glucose level recorded in the patient's medical record. Then the function f[1] ({D[j]})=D[1], and P[1]=D[1]. Parameter P[2] may measure the health condition of the patient's feet, which may be defined to depend on parameters such as blood glucose level (D[1]), the time between doctor checkups (D[2]), and some other parameter D[j]. Then P[2]=f[2]{D[j]}=f[2](D[1], D[2], D[j]), wherein the exact form of the function f[2] is specified by the generalized health model.

Using the set of parameters {P[k]} and a generalized display model of the patient, the processing means generates a personalized display model of the patient. The personalized display model preferably comprises an HTML file encoding a display comprising a body image. Generating displays using HTML is well known in the art, and will not be discussed here in detail. The formatting of. the body image is preferably customized to the targeted patient, such that the patient identifies with the body image. A set of the characteristics of the body image matches a set of predetermined characteristics. In particular, body image characteristics preferably match physical characteristics chosen by the patient. Such characteristics include age, height, gender, weight and/or build, skin color, hair color, and identity (if any) of a fictional character. In one embodiment, the body image is a schematic figure representing the patient. In other embodiments, the body image is a reproduction (e.g., a photograph) of the patient's appearance, a representation of a cartoon or fictional character, or a representation of a character in a field of interest of the patient (e.g., a favorite basketball player or movie actor).

The body image illustrates the personalized health model of the patient. In particular, the body image comprises sections assigned to body parts/organs of the patient. The image sections graphically represents the health conditions of the corresponding patient parts. Particular characteristics (e.g., color, shape, blinking rate) of the image sections are determined by the set of values {P[k]}. In general, each section of the body is assigned to at least one parameter P[k]. The body image is preferably an image map, such that the patient can access information on a body part or organ by clicking on the corresponding section of the body image.

In an embodiment suitable for the treatment of a diabetes patient, an unacceptable value of a parameter measuring a health condition of the patient's feet leads to a display of swollen feet on the body. The body's feet blink if the time period since the last doctor checkup is longer than a predetermined threshold. In an embodiment suitable for dental hygiene education, the teeth in the body image are represented to be black if a value P[k] measuring a health condition of the patients' teeth is below a predetermined threshold. The appearance of the entire body is used to characterize the personal health condition of the patient. For example, for a patient having low blood glucose levels the corresponding body is displayed to be tired.

In an embodiment used for simulating the effects of hypothetical health decisions or events on the patient's health condition, the data set {D[j]} includes a subset of simulation data characterizing a simulated personal health condition of the patient. The displayed body then contains information on the simulated health condition of the patient. The simulation can be used by the patient to examine, among others, the effects of hypothetical changes in behavior (e.g., diet and sleep patterns) on the patient's health condition.

FIG. 3 shows schematically an alternative system for delivering personalized health information, according to the present invention. A personal computer at the patient's home comprises aggregation, processing and display means. The computer keyboard is an input. Other inputs are at a remote location, and are in communication with the computer over a remote network. An HTML page illustrating the patient's personalized health model is generated on the patient's computer by the processing means.

A particular user interface of a system of the present invention is illustrated in FIGS. 4 and 5. FIGS. 4-A through 4-E illustrate the functions provided by Health Avatar™, a diabetes management application. FIGS. 5-A through 5-G are schematic depictions of screen shots from the same application, illustrating the functions of the application.

As shown in FIG. 4-A, a setup wizard is used by the patient to customize the appearance of the body image, and to enter configuration information for hardware and software in communication with the application. Hardware includes a blood glucose meter, a modem, a printer, while software includes a communications applications for communicating with health and service providers.

The body image itself (the Health Avatar™) displays actual or simulated health information of the patient, according to actual or simulated health data (see FIG. 4-B). The patient can use a blood glucose center (FIG. 4-C) to download information from a blood glucose meter, to transfer blood glucose data to the service provider database, to transfer blood glucose data to a logbook, and to display current blood glucose levels or a history of blood glucose levels. A log book (FIG. 4-D) allows the patient to access and modify records of medication, symptoms/events, lab tests, treatment plans, diets, and appointment and checkup schedules. A mail center (FIG. 4-E) is used by the patient to download treatment directions from the health provider, to transfer log book contents to the service provider and/or the health provider, and to communicate by email with the health provider.

FIG. 5-A is a schematic depiction of a screen shot 90 of the Health Avatar™ application. The display comprises several sections: a body image section 100, a log book section 102, a blood glucose center section 104, a feedback section 106, and a mail center section 108. The patient accesses functions of the application by clicking on corresponding display sections or subsections.

The functions of the log book module become accessible if the patient clicks on log book section 102, as illustrated in FIG. 5-B. A similar display (not shown) is generated if the patient clicks on blood glucose center section 104. FIG. 5-C illustrates the display after the patient accesses the "Display Blood Glucose Level" (see FIG. 4-C) subfunction of the blood glucose center. Feedback section 106 enables the patient to record information about his or her health habits.

Body image 100 comprises subsections corresponding to the patient's organs and/or body parts. If a particular body part of the patient requires attention or care, the corresponding subsection of body image 100 is highlighted. FIG. 5-D depicts the application display if the diabetes patient neglects care of his or her feet. A display subsection corresponding to the patient's feet blinks, and the patient is prompted to make an appointment with a care provider.

The overall appearance of body image section 100 depends on the blood glucose level of the patient, and on the time since the last recording of the patient's blood glucose level. FIG.

5-E illustrates the application display if the patient fails to record or download his or her blood glucose levels according to a treatment plan.

FIG. 5-F schematically depicts the application display if the patient clicks on a subsection of body image 100 corresponding to the patient's heart. The patient can request general information about the heart in diabetes patients, about the current and historical conditions of his or her heart, and about other patients approaches to the hearts' care.

It will be clear to one skilled in the art that the above embodiment may be altered in many ways without departing from the scope of the invention. For example, many relative placements of the aggregation, processing, and display means may be suitable in a system of the present invention. In particular, the data aggregation means may be in communication with the processing means over a remote network. Suitable parameters, data sets, and processing functions can be readily determined by the skilled artisan for various applications. Systems and methods of the present invention are suitable for the management of any chronic disease or condition requiring regular medical attention and patient compliance with a treatment plan, including diabetes, asthma, AIDS, heart and cardiovascular disease, weight control programs, mental health conditions, attention deficit disorder, smoking, and substance abuse. Many display and patient input implementations, including non-HTML-based implementations, can be suitable for use with the present invention. Accordingly, the scope of the invention should be determined by the following claims and their legal equivalents.

The invention claimed is:

1. A method of displaying a customized image representing an individual, comprising the steps of:
    (A) generating a health model of said individual using a computer, as a function of a data set selected from a log of data comprising one or more of medication data, symptoms, events, treatment plans, lab tests, diets, appointment schedule, and checkup schedule;
    (B) the computer generating said customized image based on said health model, said customized image corresponding to at least one body part of said individual and at least one icon related to health information of said individual, wherein (i) said at least one icon appears and highlights said at least one body part when the body part corresponding to a portion of said customized image has information to be displayed and (ii) said customized image displays current and historical conditions for one of said body parts in response to activating said at least one icon; and
    (C) displaying said customized image on a display connected to the computer.

2. The method according to claim 1, wherein said customized image further defines a feedback mechanism comprising a plurality of buttons corresponding to a plurality of behaviors of said individual.

3. The method according to claim 1, further comprising the step of:
    generating a pop-up window on said display in response to a user selection of said icon.

4. The method according to claim 3, wherein said icon comprises a log book icon.

5. The method according to claim 4, wherein said pop-up window associated with said log book icon comprises one or more buttons corresponding to one or more of (i) medication, (ii) events, (iii) lab tests, (iv) appointments and (v) checkup schedules.

6. The method according to claim 3, wherein said icon comprises one or more parameter icons.

7. The method according to claim 6, wherein said parameter icons correspond to one or more of (i) a blood glucose level, (ii) a respiratory flow, (iii) a blood pressure, (iv) a cholesterol level, (v) a patient weight, (vi) a T-cell count, (vii) a frequency of episodes, (viii) a compliance with treatment, (ix) a compliance with monitoring and (x) one or more body part conditions.

8. The method according to claim 3, wherein said icon comprises a mail icon.

9. The method according to claim 8, wherein said pop-up window corresponding to said mail icon contains one or more buttons corresponding to one or more of (i) sending email, (ii) receiving email, (iii) downloading treatment directions and (iv) transferring a log book to a service provider.

10. The method according to claim 3, wherein said pop-up window illustrates a portion of said data set in a graphical form.

11. The method according to claim 1, wherein said customized image comprises a plurality of appearances illustrating a plurality of conditions of said individual based on said health model.

12. The method according to claim 1, wherein said customized image further defines one or more highlight regions corresponding to the at least one body part.

13. The method according to claim 12, wherein said customized image further defines one or more pop-up windows associated with said highlight regions.

14. The method according to claim 13, wherein each of said pop-up windows comprises a plurality of user selectable buttons, each of said buttons corresponding to a particular aspect of said health information.

15. The method according to claim 1, wherein said customized image comprises one or more of (i) a schematic figure representation, (ii) a reproduction of an appearance of said individual, (iii) a representation of a cartoon, (iv) a representation of a fictional character and (v) a representation of a character in a field of interest of said individual.

16. A system comprising:
    a processor configured to (i) generate a health model of an individual using a computer as a function of a data set selected from a log of data comprising one or more of medication data, symptoms, events, treatment plans, lab tests, diets, appointment schedule, and checkup schedule and (ii) generate an image customized based on said health model, said customized image corresponding to at least one body part of said individual and at least one icon related to health information of said individual, wherein (i) said at least one icon appears and highlights said at least one body part when the body part corresponding to a portion of said customized image has information to be displayed and (ii) said customized image displays current and historical conditions for one of said body parts in response to activating said at least one icon; and
    a display configured to present said customized image.

17. The system according to claim 16, further comprising an aggregator configured to generate said data set.

18. The system according to claim 17, wherein said aggregator generates said data set based on one or more of (i) customization data of said display, (ii) medical records, (iii) formularies, (iv) standards of care, (v) prescribed treatment, (vi) a health profile and (vii) simulation data.

19. The system according to claim 18, wherein said display is remotely located from said aggregator.

* * * * *